US009733188B2

(12) United States Patent
Astier et al.

(10) Patent No.: US 9,733,188 B2
(45) Date of Patent: Aug. 15, 2017

(54) ENHANCING ON-CHIP FLUORESCENCE DETECTION

(71) Applicant: International Business Machines Corporation, Armonk, NY (US)

(72) Inventors: Yann Andre Nicolas Astier, Irvington, NY (US); Ning Li, White Plains, NY (US); Devendra K. Sadana, Pleasantville, NY (US); Chao Wang, Chandler, AZ (US)

(73) Assignee: International Business Machines Corporation, Armonk, NY (US)

( * ) Notice: Subject to any disclaimer, the term of this patent is extended or adjusted under 35 U.S.C. 154(b) by 81 days.

(21) Appl. No.: 14/859,608

(22) Filed: Sep. 21, 2015

(65) Prior Publication Data

US 2017/0082548 A1    Mar. 23, 2017

(51) Int. Cl.
*G01N 21/64* (2006.01)
*G01N 21/05* (2006.01)

(52) U.S. Cl.
CPC ......... *G01N 21/6486* (2013.01); *G01N 21/05* (2013.01); *G01N 2201/068* (2013.01); *G01N 2201/0686* (2013.01)

(58) Field of Classification Search
CPC .................................................. G01N 21/6486
See application file for complete search history.

(56) References Cited

U.S. PATENT DOCUMENTS

| 5,132,843 | A | 7/1992 | Aoyama et al. |
| 7,869,032 | B2 | 1/2011 | Zhang et al. |
| 8,357,980 | B2 | 1/2013 | Williams et al. |
| 8,520,202 | B2 | 8/2013 | Li |
| 2008/0019866 | A1* | 1/2008 | Paek ................. B01L 3/502707 422/400 |
| 2008/0246961 | A1* | 10/2008 | Zhang ................... B82Y 20/00 356/317 |
| 2009/0023202 | A1* | 1/2009 | Narahara ........... G01N 21/6428 435/287.9 |

(Continued)

FOREIGN PATENT DOCUMENTS

| AT | WO 2013171197 A1 * | 11/2013 | ........... G01N 21/648 |
| JP | 2009128362 A | 6/2009 | |

(Continued)

OTHER PUBLICATIONS

English translation for Japanese Application No. JP2015072481A.

(Continued)

*Primary Examiner* — David Porta
*Assistant Examiner* — Jeremy S Valentiner
(74) *Attorney, Agent, or Firm* — Vazken Alexanian; Ryan, Mason & Lewis, LLP

(57) ABSTRACT

Apparatus for enhancing on-chip fluorescence detection. For example, an apparatus comprises a microfluidic channel, an excitation signal enhancing structure formed on a first side of the microfluidic channel and a photodetector structure formed on a second side of the microfluidic channel. For example, the excitation signal enhancing structure enhances an excitation signal and the enhanced excitation signal excites one or more samples in the microfluidic channel to emit signals at a fluorescence wavelength at a higher rate.

20 Claims, 3 Drawing Sheets

(56) References Cited

U.S. PATENT DOCUMENTS

| | | | |
|---|---|---|---|
| 2009/0140128 A1* | 6/2009 | Oldham | G01N 21/648 250/216 |
| 2009/0244542 A1* | 10/2009 | Cho | G01N 21/553 356/445 |
| 2012/0105962 A1 | 5/2012 | Fattal et al. | |
| 2012/0245047 A1 | 9/2012 | Craighead et al. | |
| 2013/0222547 A1* | 8/2013 | Van Rooyen | G02B 21/0004 348/46 |
| 2013/0236982 A1 | 9/2013 | Bakker et al. | |
| 2014/0045209 A1* | 2/2014 | Chou | G01N 21/6452 435/34 |
| 2015/0024968 A1 | 1/2015 | Rulison et al. | |
| 2015/0064699 A1 | 3/2015 | Wietzorrek | |

FOREIGN PATENT DOCUMENTS

| | | | |
|---|---|---|---|
| JP | 2015072481 A | 4/2015 | |
| WO | 2009038791 A1 | 3/2009 | |
| WO | 2012061797 A2 | 5/2012 | |
| WO | 2013171197 A1 | 11/2013 | |

OTHER PUBLICATIONS

English translation for Japanese Application No. JP2009128362A.
M. Yao et al., "Highly Sensitive and Miniaturized Fluorescence Detection System with an Autonomous Capillary Fluid Manipulation Chip," Micromachines, May 2012, pp. 462-479, vol. 3, No. 2.
S. Pennathur et al., "Improving Fluorescence Detection in Lab on Chip Devices," Lab Chip, May 2008, pp. 649-652, vol. 8, No. 5.

\* cited by examiner

100

200

200

ENHANCING ON-CHIP FLUORESCENCE DETECTION

BACKGROUND

Fluorescence detection is widely used in sensing applications. Fluorescence detection is a primary technique used in lab-on-chip devices for use in, for example, medical diagnostics. On-chip fluorescence detection is desirable for portable applications. However, on-chip fluorescence detection is typically challenging due to the weakness of the signal collected.

SUMMARY

Embodiments provide an apparatus and methods for enhancing on-chip florescence detection by using an excitation signal enhancing structure. For example, in one embodiment, an apparatus comprises a microfluidic channel, an excitation signal enhancing structure formed on a first side of the microfluidic channel and a photodetector structure formed on a second side of the microfluidic structure. The excitation signal enhancing structure enhances an excitation signal.

Advantageously, in illustrative embodiments, the excitation signal enhancing structure enhances the excitation signal and the enhanced excitation signal excites one or more samples in the microfluidic channel to emit signals at a fluorescence wavelength at a higher rate.

DETAILED DESCRIPTION

Embodiments will now be described in further detail with regard to techniques for enhancing on-chip fluorescence detection. It is to be understood that various layers, structures, and/or regions shown in the accompanying drawings are schematic illustrations that are not necessarily drawn to scale. In addition, for ease of explanation, one or more layers, structures, and regions of a type commonly used to form semiconductor devices or structures may not be explicitly shown in a given drawing. This does not imply that any layer, structure, and region not explicitly shown are omitted from the actual devices.

Furthermore, it is to be understood that embodiments discussed herein are not limited to the particular materials, features, and processing steps shown and described herein. In particular, with formation (fabricating or processing) steps, it is to be emphasized that the descriptions provided herein are not intended to encompass all of the steps that may be used to form a functional integrated circuit device. Rather, certain steps that are commonly used in forming such devices, such as, for example, but not limited to, wet cleaning and annealing steps, are purposefully not described herein for economy of description.

Moreover, the same or similar reference numbers are used throughout the drawings to denote the same or similar features, elements, layers, regions, or structures, and thus, a detailed explanation of the same or similar features, elements, layers, regions, or structures will not be repeated for each of the drawings. It is to be understood that the terms "about" or "substantially" as used herein with regard to thicknesses, widths, percentages, ranges, etc., are meant to denote being close or approximate to, but not exactly. For example, the term "about" or "substantially" as used herein implies that a small margin of error is present such as, by way of example, 1% or less than the stated amount. Also, in the figures, the illustrated scale of one layer, structure, and/or region relative to another layer, structure, and/or region is not necessarily intended to represent actual scale.

A number of different illustrative embodiments for enhancing fluorescence detection on a semiconductor chip will be described below with reference to FIGS. 1 through 3B. Each of the figures illustrate steps which may be used in the process of forming an apparatus which provides for enhancing fluorescence detection on a semiconductor chip.

Figure 1:
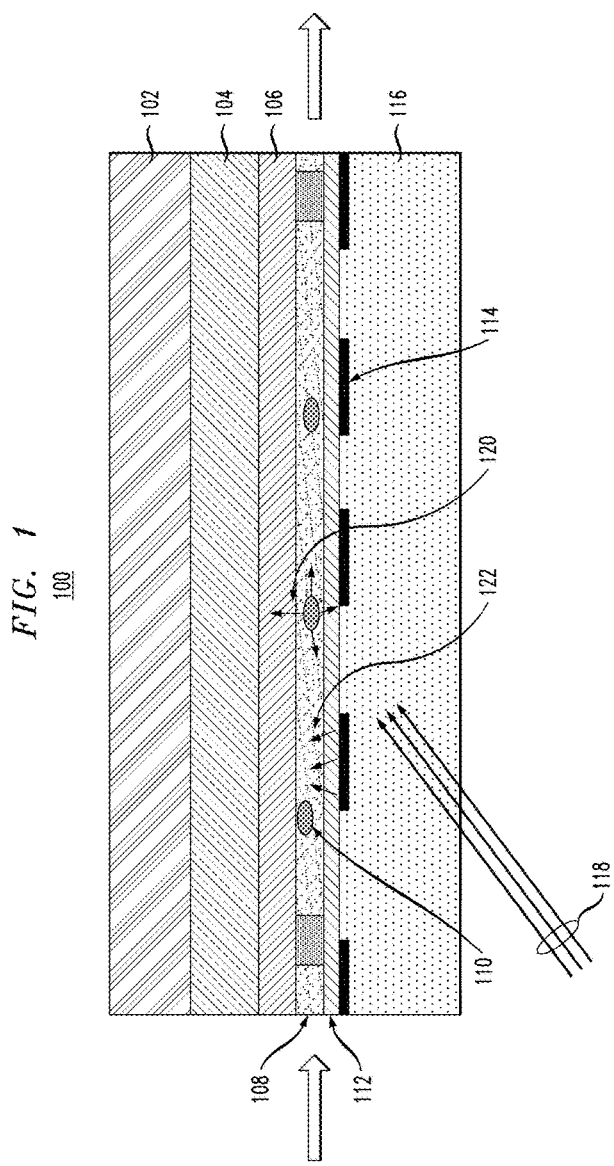
FIG. 1 illustrates a semiconductor device comprising an excitation signal enhancing structure comprising a set of plasmonic metal parallel strips to enhance an excitation signal, according to a first embodiment of the invention.

FIG. 1 illustrates an apparatus 100 providing fluorescence detection on a semiconductor chip. The apparatus 100 comprises a silicon substrate 102, on which a photodetector structure 104 is formed. The photodetector structure 104 may comprise, for example, an array of charge coupled devices (CCDs) or any other types of photodetectors operative to respond to fluorescence wavelengths. The apparatus 100 further comprises an optical filter 106 formed in front of the photodetector structure 104. The optical filter 106 may comprise, but is not limited to, a high extinction optical filter which allows fluorescence wavelengths to pass through to the photodetector structure 104 while reflecting the wavelengths of an excitation signal. The apparatus 100 further comprises a microfluidic channel 108 containing one or more samples 110 flowing therein. The direction of the flow is indicated by the bold arrows in FIG. 1. The microfluidic channel 108 is configured between the optical filter 106 and an excitation signal enhancing structure 114. Such configuration of the microfluidic channel 108 and the excitation signal enhancing structure 114 allows for minimum blockage of fluorescence emission by the samples in the microfluidic channel 108.

The apparatus 100 further comprises a thin dielectric layer 112 separating the samples in the microfluidic channel 108 from the excitation signal enhancing structure 114. The dielectric layer 112 may have a thickness ranging from about 5 nanometer (nm) to 25 nm, e.g., 10 nm, and may comprise, but not be limited to, silicon nitride or aluminum oxide. As will be described in greater detail below, the thickness of the dielectric layer 112 can effect enhancing fluorescence detection.

The apparatus 100 further comprises a glass substrate 116 operative to receive a set of excitation signals 118. The set of excitation signals 118, which may be generated by, for example, an LED light source or laser, pass through glass substrate 116 and toward the excitation signal enhancing structure 114. Some of the excitation signals 118 may reach the samples 110 flowing in the microfluidic channel 108 directly, while others reach the excitation signal enhancing structure 114. Once the samples 110 are excited, they emit signals at a fluorescence wavelength 120 which pass through the optical filter 106 and are detected by the photodetector structure 104.

In FIG. 1, the excitation signal enhancing structure 114 is a plasmonic metal structure. Enhancing fluorescence detection in this embodiment exploits a special characteristic of the plasmonic metals. More specifically, the plasmonic metals, in response to incident excitation signals, emit resonant electromagnetic waves. Compared with the incident signals, the resonant signals exhibit a much higher intensity. Thus, in FIG. 1, when a set of excitation signals 118 enter through the glass substrate 116, some of the excitation signals will reach a set of parallel plasmonic metal strips of the excitation signal enhancing structure 114 while others pass through the excitation signal enhancing structure 114 through the open spaces in between the plasmonic metal strips. The set of excitation signals 118 that reach the plasmonic metal strips excite surface plasmons on the plasmonic metal strips and cause them to propagate intensified resonant signals. When the resonant signals of higher intensity reach the samples 110 flowing in the microfluidic channel 108, the samples' fluorescence emission rate is greatly enhanced.

However, these strong-intensity resonant signals are generally local to the plasmonic metal strips and necessitate the samples 110 to flow in close proximity to the excitation signal enhancing structure 114. Additionally, the samples 110 flowing in the microfluidic channel 108 should not be in direct contact with the plasmonic metal strips. Consequently, the thin dielectric layer 112 in FIG. 1 avoids these issues by providing separation and maintains enhanced fluorescence emission rate.

Figure 2A:
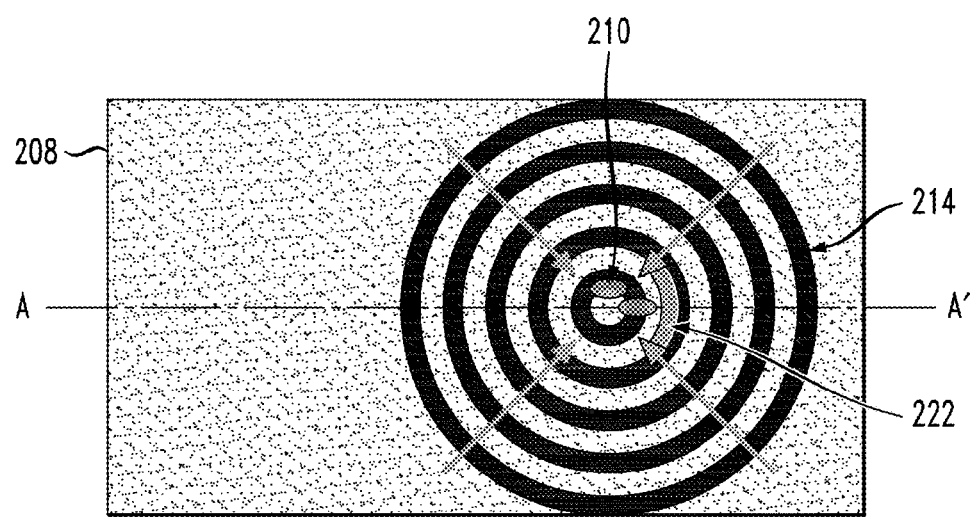
FIG. 2A illustrates a top view of a semiconductor device comprising an excitation signal enhancing structure comprising a set of plasmonic metal concentric rings, according to a second embodiment of the invention.
Figure 2B:
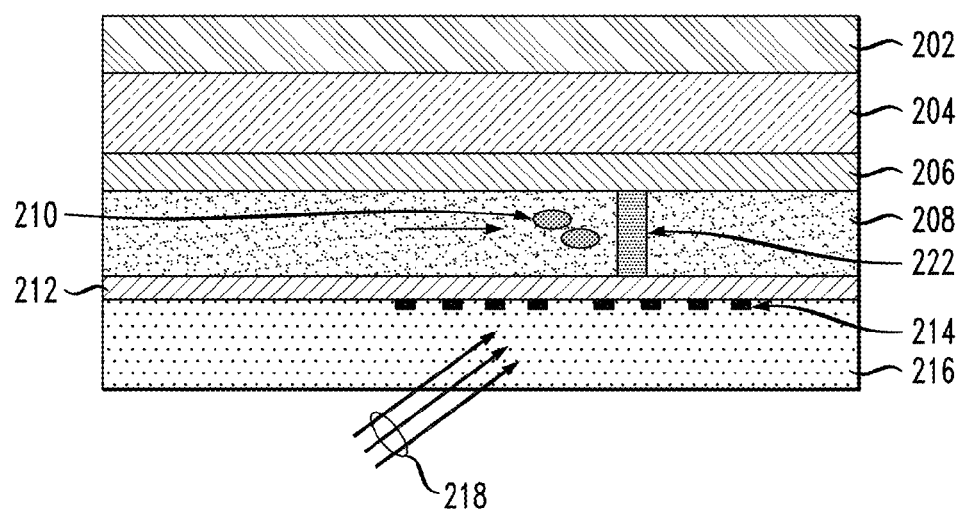
FIG. 2B illustrates a cross-sectional side view of FIG. 2A, according to the second embodiment of the invention.

FIGS. 2A and 2B shows another embodiment wherein an excitation signal enhancing structure is a plasmonic metal structure, but in a form of a set of concentric rings. As will be explained below, the concentric-rings formation provides for additional excitation signal enhancement.

FIG. 2A is a top view of an apparatus 200. FIG. 2A shows a microfluidic channel 208, one or more samples 210 flowing in the microfluidic channel 208, and an excitation signal enhancing structure 214. The microfluidic channel 208 is formed above a dielectric layer 212 (not shown in FIG. 2A) and the excitation signal enhancing structure 214. FIG. 2B is a cross-sectional side view of the apparatus 200 along the AA' axis shown in FIG. 2A. FIG. 2B illustrates the apparatus 200 further comprising a silicon substrate 202, a photodetector structure 204, an optical filter 206, a dielectric layer 212 and a glass substrate 216.

As shown in FIG. 2A, the excitation signal enhancing structure 214 is a set of plasmonic metal concentric rings (in FIG. 2B, the cross-sectional side view shows the set of concentric rings as a set of discrete strips). A distinct advantage of using a set of concentric rings as the excitation signal enhancing structure formation is that such formation provides for a grating lens effect. FIG. 2B shows a set of excitation signals 218 entering through glass substrate 216. As described with respect to FIG. 1, some of the excitation signals will pass through excitation signal enhancing structure 214 while others reach the plasmonic metal surface of the excitation signal enhancing structure 214. The set of excitation signals 218 that excites surface plasmons on the plasmonic metals of the excitation signal enhancing structure 214 will cause them to propagate intensified resonant signals. As indicated by the four white arrows in FIG. 2A, any signal passing through the rings and out from the plasmonic metal surface of the excitation signal enhancing structure 214 are focused toward the center. This results in both the excitation signals 218 and the resonant signals (not shown in FIG. 2A) to be focused centrally to a small region.

The apparatus 200 further comprises a sample stopper 222, formed vertically through microfluidic channel 208, between the dielectric layer 212 and an optical filter 206. The sample stopper 222, which may comprise, but not be limited to, silicon-nitride or any dielectric non-metals, forms an arc operative to increase the concentration of the samples 210 flowing in the microfluidic channel 208 at the vicinity of the sample stopper 222. The combination of the sample stopper 222 concentrating the samples 210 at the center and the concentric rings structure of the excitation signal enhancing structure 214 focusing both the excitation signals 218 and the resonant signals (not shown in FIG. 2A) results in an even stronger emission of signals at a fluorescence wavelength from the samples 210.

Figure 3A:
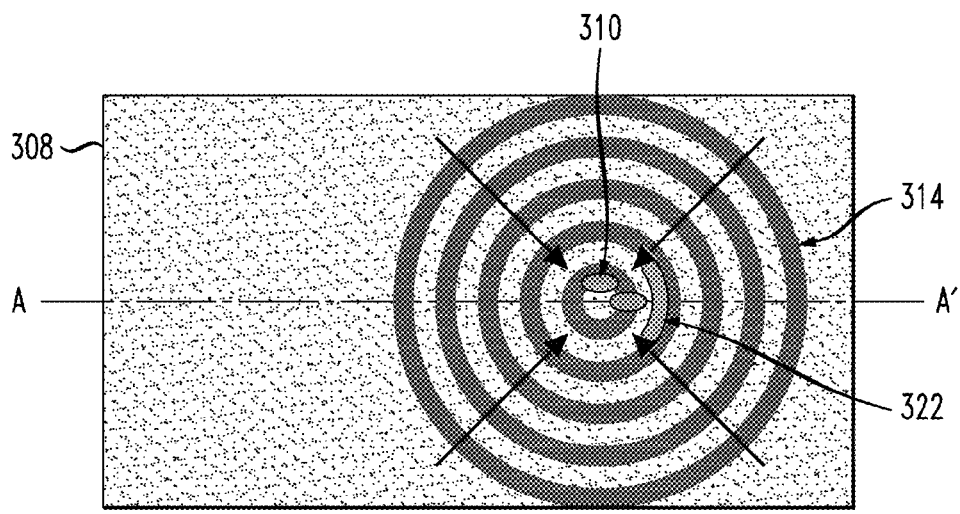
FIG. 3A illustrates a top view of a semiconductor device comprising an excitation signal enhancing structure comprising a set of dielectric concentric rings, according to a third embodiment of the invention.
Figure 3B:
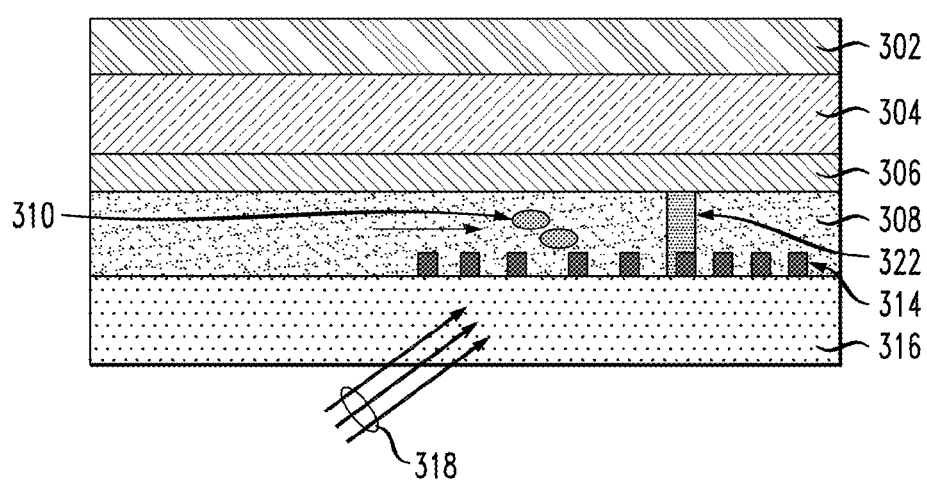
FIG. 3B illustrates a cross-sectional side view of FIG. 3A, according to the third embodiment of the invention.

FIGS. 3A and 3B shows yet another embodiment comprising an excitation signal enhancing structure but this time, the excitation signal enhancing structure is a set of dielectric concentric rings. Dielectric concentric rings may comprise, but not be limited to, silicon nitride or aluminum oxide.

FIG. 3A shows a top view of an apparatus 300 and FIG. 3B is a cross-sectional side view of the apparatus 300 along the AA' axis shown in FIG. 3A. The apparatus 300 comprises a silicon substrate 302, a photodetector structure 304, an optical filter 306, a microfluidic channel 308, one or more samples 310 in the microfluidic channel 308, a glass substrate 316 and a sample stopper 322. These elements of the apparatus 300 are substantially similar and perform substantially the similar functions to the similarly referenced elements in the apparatus 200 shown in FIGS. 2A and 2B. The apparatus 300 differs from the apparatus 200 in that the apparatus 300 comprises an excitation signal enhancing structure 314 which is a set of dielectric concentric rings and the excitation signal enhancing structure 314 is formed directly inside the microfluidic channel 308. In this embodiment, a set of excitation signals 318 enter through the glass substrate 316 and travel toward the excitation signal enhancing structure 314. Some of the excitation signals 318 will come in contact with the excitation signal enhancing structure 314 while others pass the excitation signal enhancing structure 314 without striking the structure. In this embodiment, there is no plasmonic metal enhancement of the excitation signals by emission of resonant signals. However, the use of a set of dielectric concentric rings structure nevertheless produces a grating lens effect by focusing a set of excitation signals 318 passing through the dielectric concentric rings toward the center. Enhancing of the fluorescence detection is achieved through the focusing of the excitation signals 318 onto the samples 310 stopped by the sample stopper 322, resulting in a higher emission rate of fluorescence wavelengths by the samples 310.

It is to be understood that the methods discussed herein for fabricating semiconductor structures can be incorporated within semiconductor processing flows for fabricating other types of semiconductor devices and integrated circuits with various analog and digital circuitry or mixed-signal circuitry. In particular, integrated circuit dies can be fabricated with various devices such as transistors, diodes, capacitors, inductors, etc. An integrated circuit in accordance with embodiments can be employed in applications, hardware, and/or electronic systems. Suitable hardware and systems for implementing the invention may include, but are not limited to, personal computers, communication networks, electronic commerce systems, portable communications devices (e.g., cell phones), solid-state media storage devices, functional circuitry, etc. Systems and hardware incorporating such integrated circuits are considered part of the embodiments described herein.

Furthermore, various layers, regions, and/or structures described above may be implemented in integrated circuits (chips). The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multichip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

Although illustrative embodiments have been described herein with reference to the accompanying drawings, it is to be understood that the invention is not limited to those precise embodiments, and that various other changes and modifications may be made by one skilled in art without departing from the scope or spirit of the invention.

What is claimed is:

1. An apparatus for signal detection, comprising:
   an excitation signal enhancing structure configured to generate an enhanced excitation signal in response to receipt of an incident excitation signal comprising electromagnetic radiation, wherein the enhanced excitation signal exhibits an intensity that is higher than an intensity of the incident excitation signal;
   a dielectric layer comprising a first side and a second side, wherein the excitation signal enhancing structure is formed on the first side of the dielectric layer;
   a microfluidic channel comprising a first side and a second side, wherein the first side of the microfluidic channel is formed on the second side of the dielectric layer, and wherein the microfluidic channel comprises one or more samples configured to emit one or more fluorescence response signals in response to being excited by the enhanced excitation signal;
   wherein the dielectric layer separates the one or more samples from the excitation signal enhancing structure;
   an optical filter comprising a first side and a side second, wherein the first side of the optical filter is formed on the second side of the microfluidic channel; and
   a photodetector structure formed on the second side of the optical filter;
   wherein the optical filter is configured to reflect the incident excitation signal and allow passage of the one or more fluorescence response signals to the photodetector structure.

2. The apparatus of claim 1, wherein the excitation signal enhancing structure is a plasmonic metal structure.

3. The apparatus of claim 2, wherein the enhanced excitation signal is a resonant signal emitted by the plasmonic metal structure in response to receipt of the incident excitation signal.

4. The apparatus of claim 3, wherein the plasmonic metal structure is a set of plasmonic metal concentric rings.

5. The apparatus of claim 4, wherein at least one of the incident excitation signal and the resonant signal is focused toward a center of the set of plasmonic metal concentric rings.

6. The apparatus of claim 5, further comprising a sample stopper formed through the microfluidic channel, wherein the sample stopper is operative to increase sample concentration of the one or more samples in a vicinity of the sample stopper.

7. The apparatus of claim 1, wherein the excitation signal enhancing structure is a set of dielectric concentric rings, and wherein the incident excitation signal is focused toward a center of the set of dielectric concentric rings.

8. The apparatus of claim 1, further comprising a glass substrate formed on the first side of the dielectric layer, wherein the excitation signal enhancing structure is formed on the glass substrate.

9. A method for forming a signal detection apparatus comprising:
   forming a dielectric layer comprising a first side and a second side;
   forming an excitation signal enhancing structure on the first side of the dielectric layer;
   forming a microfluidic channel comprising a first side and a second side, wherein the first side of the microfluidic channel is formed on the second side of the dielectric layer;
   forming an optical filter comprising a first side and a second side, wherein the first side of the optical filter is formed on the second side of the microfluidic channel; and
   forming a photodetector structure on the second side of the microfluidic channel;
   wherein the excitation signal enhancing structure is configured to generate an enhanced excitation signal in response to receipt of an incident excitation signal comprising electromagnetic radiation, and wherein the enhanced excitation signal exhibits an intensity that is higher than an intensity of the incident excitation signal;
   wherein the microfluidic channel comprises one or more samples configured to emit one or more fluorescence response signals in response to being excited by the enhanced excitation signal;
   wherein the dielectric layer separates the one or more samples from the excitation signal enhancing structure; and
   wherein the optical filter is configured to reflect the incident excitation signal and allow passage of the one or more fluorescence response signals to the photodetector structure.

10. The method of claim 9, wherein the excitation signal enhancing structure is a plasmonic metal structure.

11. The method of claim 10, wherein the enhanced excitation signal is a resonant signal emitted by the plasmonic metal structure in response to receipt of the incident excitation signal.

12. The method of claim 11, wherein the plasmonic metal structure is a set of plasmonic metal concentric rings.

13. The method of claim 12, wherein at least one of the incident excitation signal and the resonant signal is focused toward a center of the set of plasmonic metal concentric rings.

14. The method of claim 9, wherein the excitation signal enhancing structure is a set of dielectric concentric rings, and wherein the incident excitation signal is focused toward a center of the set of dielectric concentric rings.

15. The method of claim 9, further comprising forming a sample stopper through the microfluidic channel, wherein the sample stopper is operative to increase sample concentration of the one or more samples in a vicinity of the sample stopper.

16. The method of claim 9, further comprising forming a glass substrate on the first side of the dielectric layer, wherein the excitation signal enhancing structure is formed on the glass substrate.

17. An integrated circuit for signal detection, comprising:
- an excitation signal enhancing structure configured to generate an enhanced excitation signal in response to receipt of an incident excitation signal comprising electromagnetic radiation, wherein the enhanced excitation signal exhibits an intensity that is higher than an intensity of the incident excitation signal;
- a dielectric layer comprising a first side and a second side, wherein the excitation signal enhancing structure is formed on the first side of the dielectric layer;
- a microfluidic channel comprising a first side and a second side, wherein the first side of the microfluidic channel is formed on the second side of the dielectric layer, and wherein the microfluidic channel comprises one or more samples configured to emit one or more fluorescence response signals in response to being excited by the enhanced excitation signal;
- wherein the dielectric layer separates the one or more samples from the excitation signal enhancing structure;
- an optical filter comprising a first side and a second side, wherein the first side of the optical filter is formed one the second side of the microfluidic channel;
- a photodetector structure comprising a first side and a second side, wherein the first side of the photodetector structure is formed on the second side of the optical filter;
- wherein the optical filter is configured to reflect the incident excitation signal and allow passage of the one or more fluorescence response signals to the photodetector structure; and
- a silicon substrate formed on the second side of the photodetector structure.

18. The integrated circuit of claim 17, wherein the excitation signal enhancing structure is a plasmonic metal structure, and wherein the enhanced excitation signal is a resonant signal emitted by the plasmonic metal structure in response to receipt of the incident excitation signal.

19. The integrated circuit of claim 17, further comprising a sample stopper formed through the microfluidic channel and a glass substrate formed on the first side of the dielectric layer, wherein the sample stopper is operative to increase sample concentration of the one or more samples in a vicinity of the sample stopper, and wherein the excitation signal enhancing structure is formed on the glass substrate.

20. The integrated circuit of claim 17, wherein the excitation signal enhancing structure is a set of dielectric concentric rings, and wherein the enhanced excitation signal is generated by focusing the incident excitation signal toward a center of the set of dielectric concentric rings.

* * * * *